(12) United States Patent
Kato et al.

(10) Patent No.: US 8,265,735 B2
(45) Date of Patent: Sep. 11, 2012

(54) APPARATUS AND METHOD FOR IMAGING ANTERIOR EYE PART BY OPTICAL COHERENCE TOMOGRAPHY

(75) Inventors: Chihiro Kato, Nagoya (JP); Keiichiro Okamoto, Nagoya (JP); Kenichi Hayashi, Nagoya (JP); Hiromu Watanabe, Nagoya (JP)

(73) Assignee: Tomey Corporation, Nagoya-Shi, Aichi-Ken (JP)

( * ) Notice: Subject to any disclaimer, the term of this patent is extended or adjusted under 35 U.S.C. 154(b) by 876 days.

(21) Appl. No.: 12/331,752

(22) Filed: Dec. 10, 2008

(65) Prior Publication Data

US 2009/0149742 A1 Jun. 11, 2009

(30) Foreign Application Priority Data

Dec. 11, 2007 (JP) ................................ 2007-319563

(51) Int. Cl.
*A61B 6/00* (2006.01)
(52) U.S. Cl. ....................................... 600/476; 600/473
(58) Field of Classification Search .................. 600/473, 600/476; 351/200, 206, 209
See application file for complete search history.

(56) References Cited

U.S. PATENT DOCUMENTS

| 5,491,524 | A | 2/1996 | Hellmuth et al. | |
|---|---|---|---|---|
| 5,644,642 | A * | 7/1997 | Kirschbaum | 382/103 |
| 6,741,359 | B2 * | 5/2004 | Wei et al. | 356/512 |
| 7,281,801 | B2 * | 10/2007 | Wang | 351/246 |
| 7,301,644 | B2 * | 11/2007 | Knighton et al. | 356/479 |
| 7,505,142 | B2 * | 3/2009 | Knighton et al. | 356/479 |
| 2004/0068192 | A1 * | 4/2004 | Westphal et al. | 600/476 |
| 2005/0024586 | A1 * | 2/2005 | Teiwes et al. | 351/209 |
| 2005/0270486 | A1 * | 12/2005 | Teiwes et al. | 351/209 |
| 2006/0187462 | A1 | 8/2006 | Srinivasan et al. | |
| 2007/0232861 | A1 | 10/2007 | Kohno et al. | |

FOREIGN PATENT DOCUMENTS

| JP | 08-206075 | 8/1996 |
|---|---|---|
| JP | 09-149914 | 6/1997 |
| JP | 2006-212153 | 8/2006 |
| JP | 2007-117629 | 5/2007 |
| JP | 2007-127425 | 5/2007 |
| JP | 2007-202725 | 8/2007 |
| JP | 2007-275375 | 10/2007 |
| JP | 2007268047 A | 10/2007 |
| WO | WO 2006/022045 A1 | 3/2006 |

OTHER PUBLICATIONS

European Search Report, for European Patent Application No. 08253928.9, dated Apr. 20, 2009.
Notification of Reasons for Refusal dated Nov. 15, 2011 in corresponding Japanese Patent Application No. 2007-319563.

\* cited by examiner

*Primary Examiner* — Peter Luong
(74) *Attorney, Agent, or Firm* — Thomas & Karceski, PC

(57) ABSTRACT

An optical coherence tomography (OCT) anterior eye part imaging apparatus includes a tomographic image obtaining unit obtaining a tomographic image of an anterior eye part of subject's eye in a depth direction by optical coherence tomography, an imaging unit imaging a frontal image of subject's eye, a display unit displaying the image of subject's eye, a corneal apex location detecting unit detecting a location of subject's eye, an alignment unit moving an apparatus body relative to the holder so that the location of corneal apex corresponds with a predetermined image obtaining location, a designating unit designating an area or a location where the tomographic image is obtained on subject's frontal image displayed on the display unit, and a scan line setting unit setting a scan line in the tomographic image obtaining unit on a straight line passing the corneal apex according to the designated area or location.

8 Claims, 7 Drawing Sheets

APPARATUS AND METHOD FOR IMAGING ANTERIOR EYE PART BY OPTICAL COHERENCE TOMOGRAPHY

CROSS-REFERENCE TO RELATED APPLICATIONS

This application is based upon and claims the benefit of priority from the prior Japanese Patent Application No. 2007-319563 filed on Dec. 11, 2007, the entire contents of which are incorporated herein by reference.

BACKGROUND OF THE INVENTION

1. Field of the Invention

The present invention relates to an apparatus for imaging an anterior eye part of subject's eye by optical coherence tomography (OCT), in which a tomographic image of subject's anterior eye part is obtained by the OCT and a method therefor.

2. Description of the Related Art

There have conventionally been provided optical coherence tomographic apparatus which serve as an inspection apparatus used for ophthalmic examination by optical coherence tomography (OCT) and obtaining a tomographic image of subject's eye (eyeball) by the OCT. The optical coherence tomographic apparatus includes two types, that is, a time domain type and a Fourier domain type. The time domain OCT apparatus obtains a tomographic image while a mirror is moved so that a light path length of reference light is mechanically changed. The Fourier domain OCT apparatus detects spectral information using a spectroscope in order to obtain a tomographic image. The Fourier domain OCT apparatus may include an optical frequency ramping OCT apparatus which detects a spectral interference signal using a wavelength scanning optical source in order to obtain a tomographic image.

In OCT, subject's eye is generally irradiated with measurement light so that a one-dimensional scanning is carried out, whereby a two-dimensional (2D) tomographic image is obtained (B-scan). A plurality of 2D tomographic images are obtained while a scan line is repeatedly moved relative to the subject's eye, whereby a three-dimensional (3D) tomographic image is obtained (C-scan). FIG. 5A shows a raster scan as one of scanning manners. In the raster scan, a one-dimensional scanning is carried out along a horizontally extending scan line (B-scan). The one-dimensional scanning is repeated while a scan line is vertically moved (C-scan), whereby a 3D image of eyeball is obtained. Consequently, tomographic images along the scan lines can be obtained as shown in FIG. 5B.

FIG. 6A shows a radial scan as another scanning manner. In the radial scan, a one-dimensional scanning is carried out along a radially extending scan line (B-scan). The one-dimensional scanning is repeated while the scan line is circumferentially moved (C-scan). Consequently, tomographic images taken along respective scan lines are obtained as shown in FIG. 6B.

Japanese patent application publication JP-A-2007-127425 discloses a correcting method in optical tomographic imaging method. The document discloses an ophthalmologic photography apparatus having an OCT optical system. Japanese patent application publication JP-A-2006-212153 discloses an ophthalmologic photography apparatus. Japanese patent application publication JP-A-2007-117629 discloses an ophthalmologic imaging apparatus. A 3D image is obtained in each of these documents.

The method and apparatus disclosed by the respective above-mentioned documents each necessitate a relatively longer imaging time period to obtain a 3D image of subject's eye. For example, it takes about 6 seconds to image an anterior eye part with a diameter of 16 mm. Accordingly, the subject has to keep his or her face or eyeball immobile in the meantime, which results in a large burden to the subject. When an object to be measured or subject's eye happens to move during imaging, a precise 3D image cannot be obtained. In particular, a C-scan direction image is apt to be subjected to influences of involuntary eye movement, and accordingly, an obtained tomographic image tends to be inferior in the image quality.

The first and second of the above-mentioned three documents, JP-A-2007-127425 and JP-A-2006-212153 disclose respective methods of correcting the movement of the object to be measured or subject's eye on the obtained tomographic image in a software manner. However, there is a possibility that in the occurrence of blinking or large fixation disparity, the above-described methods may result in an error of correction or display an erroneous image. More specifically, an imaging time needs to be rendered as short as possible in order that a high-precision 3D image may be obtained.

Furthermore, when an anterior eye part is imaged by an OCT imaging apparatus, measurement light is refracted on a substantially spherical cornea (a boundary between the cornea surface and an anterior chamber). As a result, an obtained tomographic image is distorted. Accordingly, the tomographic image refracted on the cornea needs to be corrected. However, since measurement light is incident from a direction differing from a normal direction of the cornea in the conventional B-scan, a tomographic image obtained by one B-scan is affected not only by the refraction on a fault surface thereof but also by the refraction on other surfaces. As a result, the tomographic image needs to be corrected with respect to the refraction on the cornea after a 3D tomographic image has been obtained by execution of C-scan. Since the processing is extremely complicated, the correction is time-consuming and has a difficulty in providing high precision.

SUMMARY OF THE INVENTION

Therefore, an object of the present invention is to provide an OCT anterior eye part imaging apparatus which obtains a tomographic image of subject's anterior eye part by the OCT method, can shorten the imaging time period, can provide a tomographic image with high resolution and can easily correct refraction of light on the cornea, and a method therefor.

To achieve the above or other objects, the present invention provides, in one aspect, an optical anterior eye part imaging apparatus, comprising a holder; an apparatus body mounted on the holder; a tomographic image obtaining unit that is provided on the apparatus body and obtains a tomographic image of subject's anterior eye part in a depth direction by the optical coherence tomography, the tomographic image being taken along a scan line; an imaging unit that is provided on the apparatus body to image a frontal image of the subject's eye; a display unit that displays the image of the subject's eye obtained by the imaging unit; a corneal apex location detecting unit that detects a location of a corneal apex of the subject's eye; an alignment unit that moves the apparatus body relative to the holder so that the location of the corneal apex corresponds with a predetermined image obtaining location; a designating unit that designates an area or a location whose tomographic image is to be obtained on the subject's frontal image displayed on the display unit; and a scan line setting unit that sets a scan line in the tomographic image obtaining unit on a straight line passing the corneal apex according to the area or location designated by the designating unit.

According to the above-described construction, the frontal image of the subject's eye taken by the imaging unit is displayed on the display unit when a tomographic image of the subject's anterior eye part is obtained. The location of the subject's corneal apex is then detected by the corneal apex location detecting unit, and the apparatus body and accordingly the tomographic image obtaining unit are moved by the alignment unit so that the location of the corneal apex of the subject's eye corresponds with the predetermined image obtaining location. In this state, the tomographic image of the subject's anterior eye part in the depth direction is obtained by the tomographic image obtaining unit. In this case, the area or location whose tomographic image is to be obtained on the frontal image of the subject's eye displayed on the display unit is previously designated by the designating unit. The scan line in the tomographic image obtaining unit is then set on a straight line passing the corneal apex according to the designated area or the location by the scan line setting unit.

Since the cornea may be considered to be spherical, the measurement light vertically enters the cornea on a straight line passing the corneal apex. Accordingly, a B-scan tomographic image taken along the scan line located on the straight line is affected by corneal refraction two-dimensionally only in the plane of the tomographic image. Consequently, the correction of tomographic image regarding corneal refraction can be executed based on the single tomographic image without obtainment of other tomographic images in a relatively shorter time period easily and precisely.

Furthermore, an object to be imaged by the tomographic image obtaining unit can be limited to a necessary part (an area or location) in designation. Consequently, a time period necessary to obtain or take a tomographic image can be reduced without reduction in the resolution. In this case, for example, a target tomographic image can be obtained when, in the diagnosis of glaucoma, an area to be imaged is limited to a corner portion that is considered to be abnormal. Since a time period necessary for imaging is reduced, a burden on the subject can be reduced, and the influence of involuntary eye movement can also be reduced.

The optical coherence tomography anterior eye part imaging apparatus may further comprise an automatic eye tracking unit that moves the apparatus body so that a predetermined locational relationship is maintained between the corneal apex and the apparatus body during the obtainment of the tomographic image by the tomographic image obtaining unit. A tomographic image is thus obtained while the locational relation between the corneal apex and the apparatus body is kept constant. Accordingly, the scan line can be prevented from being displaced from the straight line passing the corneal apex even when the subject's eye is moved.

The designating unit may comprise a touch panel provided on a screen of the display unit. Consequently, an area or location whose tomographic image is to be obtained can be designated easily and reliably.

In another aspect, the invention provides a method of obtaining a tomographic image of an anterior eye part of subject's eye for ophthalmic examination by the use of an anterior eye part imaging apparatus, said apparatus including a holder; an apparatus body mounted on the holder; a tomographic image obtaining unit that is provided on the apparatus body and obtains a tomographic image of subject's anterior eye part in a depth direction by the optical coherence tomography, the tomographic image being taken along a scan line; an imaging unit that is provided on the apparatus body to image a frontal image of the subject's eye; a display unit that displays the image of the subject's eye obtained by the imaging unit; a corneal apex location detecting unit that detects a location of a corneal apex of the subject's eye; an alignment unit that moves the apparatus body relative to the holder so that the location of the corneal apex corresponds with a predetermined image obtaining location; a designating unit that designates an area or a location whose tomographic image is to be obtained on the subject's frontal image displayed on the display unit; and a scan line setting unit that sets a scan line in the tomographic image obtaining unit on a straight line passing the corneal apex according to the area or location designated by the designating unit, the method comprising receiving input designating an area or a location whose tomographic image is to be obtained while the subject's frontal image is displayed on the display unit; setting, in an automatic manner, a scan line in the tomographic image obtaining unit on a straight line passing the corneal apex according to the area or location designated by the input; and obtaining a tomographic image by the tomographic image obtaining unit based on the scan line set in the scan line setting step.

According to the above-described method, the correction of tomographic image regarding corneal refraction can be executed based on the single tomographic image without obtainment of other tomographic images in a relatively shorter time period easily and precisely. Additionally, a time period necessary to obtain or take a tomographic image can be reduced.

In execution of the tomographic image obtaining step, the apparatus body may be moved by an automatic eye tracking unit so that a predetermined locational relationship is maintained between the corneal apex and the apparatus body during the obtainment of the tomographic image by the tomographic image obtaining unit. Consequently, the scan line can be prevented from being displaced from the straight line passing the corneal apex even when the subject's eye is moved.

Furthermore, the user may touch a touch panel provided on the screen of the display in the designating step to directly designate an area or a location whose tomographic image is to be obtained on the subject's frontal image displayed on the display unit. Consequently, an area or location where a tomographic image is to be obtained can be designated easily and reliably.

BRIEF DESCRIPTION OF THE DRAWINGS

Other objects, features and advantages of the present invention will become clear upon reviewing the following description of the embodiment with reference to the accompanying drawings, in which.

DETAILED DESCRIPTION OF THE INVENTION

Figure 1:
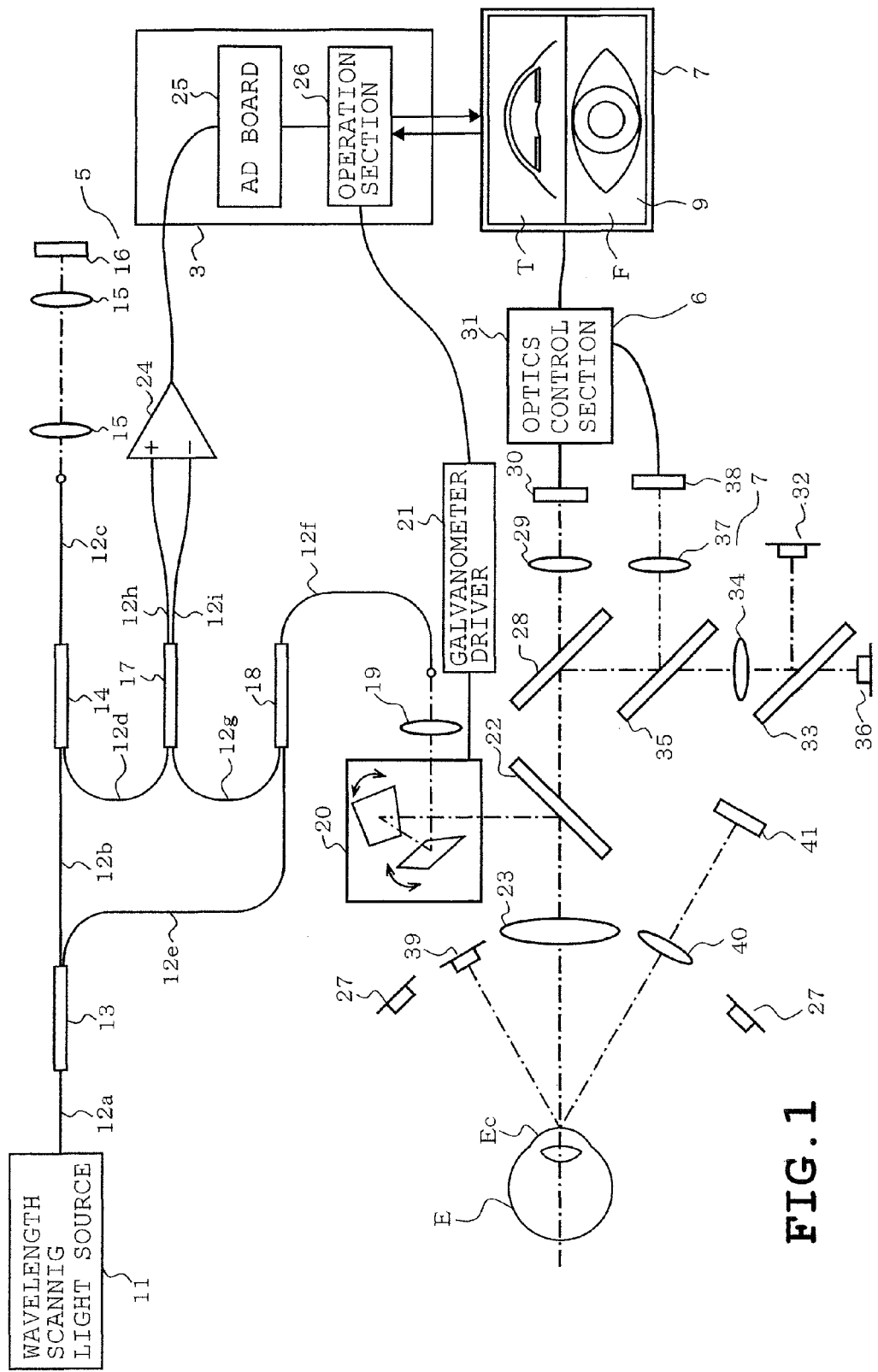
FIG. 1 is a diagram showing an arrangement of optical system of the optical coherence tomography anterior eye part imaging apparatus in accordance with one embodiment of the present invention.

An embodiment of the present invention will be described with reference to FIGS. 1 to 4 of the accompanying drawings. Referring first to FIG. 2, an electrical arrangement of an optical coherence tomography (OCT) anterior eye part imaging apparatus 1 of the embodiment is shown schematically. The OCT anterior eye part imaging apparatus 1 is used for ophthalmologic examination of an anterior eye part Ec (see FIG. 1) of subjects' eye E such as angle measurement, corneal curvature, corneal thickness distribution or depth of anterior chamber. The OCT anterior eye part imaging apparatus 1 obtains a tomographic image of the anterior eye part Ec of the subject's eye E by an optical coherence tomography method.

The OCT anterior eye part imaging apparatus 1 includes an apparatus body (not shown) which is mounted on a holder (not shown) so as to be movable in the X-direction (right-and-left direction), the Y-direction (vertical direction) and the Z-direction (front-and-rear direction). A jaw support and a forehead pad are fixedly mounted on the holder. When the subject puts his or her jaw on the jaw support and applies the forehead pad onto his or her forehead, the subject's eye E is located in front of an imaging inspection window provided in the front of the apparatus body. Light is caused to go into and out of the inspection window.

The OCT anterior eye part imaging apparatus 1 includes a body drive 2 for moving the apparatus body in the X-, Y- and Z-directions as shown only in FIG. 2. The body drive 2 comprises an X-direction moving motor, a Y-direction moving motor and a Z-direction moving motor as well known in the art. The body drive 2 is adapted to be controlled by a control device 3. The body drive 2 and the control device 3 serve as an alignment unit and an automatic eye tracking unit together with an alignment optics system 4 and the like as will be described later.

The apparatus body is provided with the control device 3 comprising a microcomputer which includes a central processing unit (CPU) and memories and controls the whole imaging apparatus. The apparatus body is further provided with an OCT system 5 serving as a tomographic image obtaining unit that obtains a tomographic image of the subject's anterior eye part Ec, an anterior eye part imaging system 6 constituting an imaging unit which images a frontal image of the subject's eye E and an alignment optics system 4. The alignment optics system 4 constitutes the alignment unit and the automatic eye tracking unit as described above and further constitutes a corneal apex location detecting unit. The OCT system 5, the anterior eye part imaging system 6 and the alignment system 4 are connected to the control device 3. These systems and device will be described in detail later.

The apparatus body is further provided with a monitor 7 serving as a display which is disposed on the rear side (subject side) to display a subject's frontal image and the like. The apparatus body is still further provided with a key operation section 8 which is operated by the inspector (operator) so that various instructions or the like are input. The key operation section 8 includes a measurement starting switch and a measured area designating switch. Furthermore, a touch panel 9 is mounted over a screen of the monitor 7. The monitor 7, the key operation section 8 and the touch panel 9 are connected to the control device 3. A storage section 10 is also connected to the control device 3. Data of an imaged three-dimensional (3D) image is stored on the storage section 10.

Figure 2:
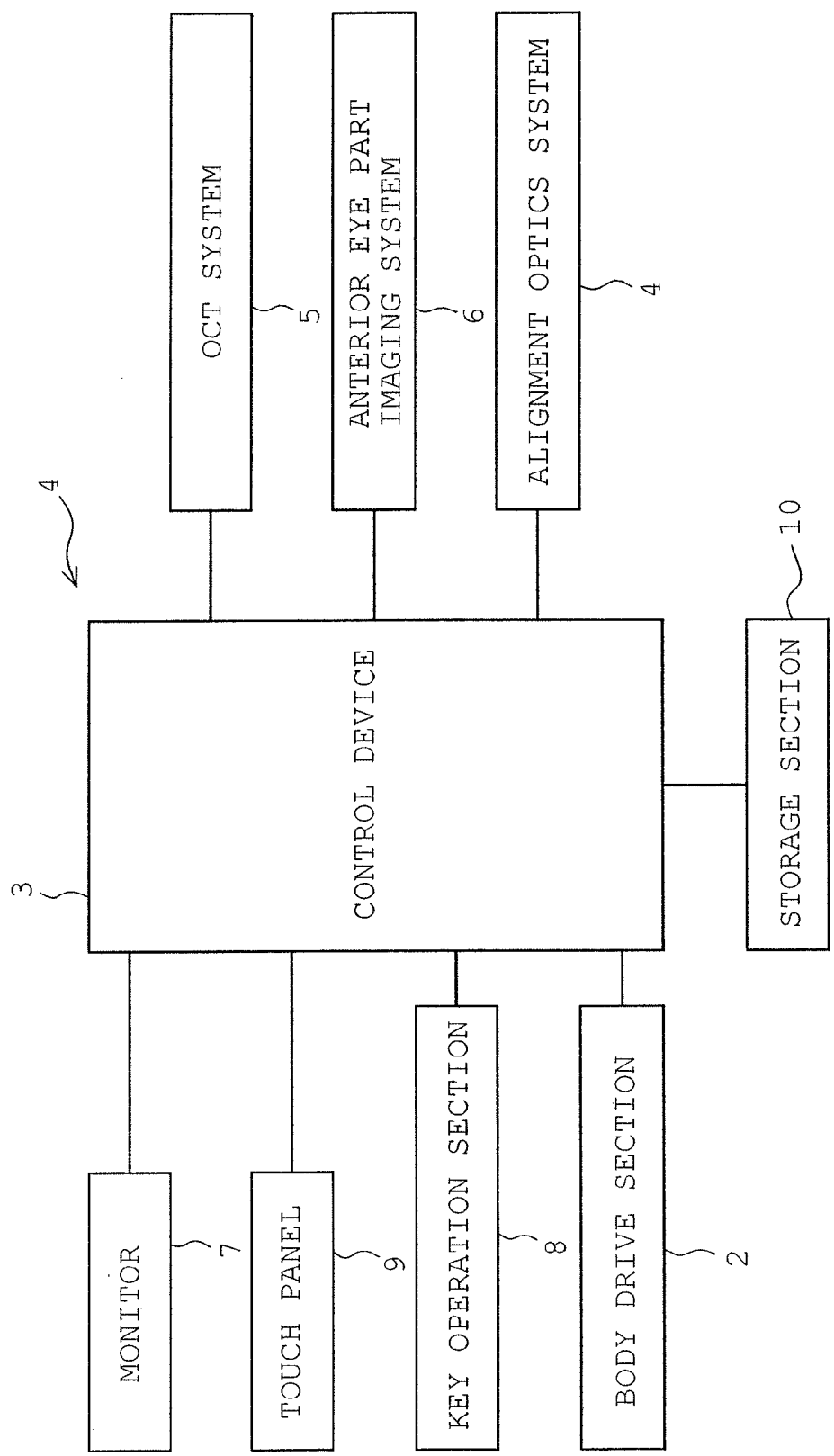
FIG. 2 is a schematic block diagram showing an electrical arrangement of the optical coherence tomography anterior eye part imaging apparatus.

Referring now to FIG. 1, the arrangement of the above-described optics system is shown. The optics system includes the OCT system 5, the anterior eye part imaging system 6, the alignment optics system 4. These systems will be described sequentially in this order. The OCT system 5 is provided for obtaining a tomographic image of the anterior eye part Ec by the optical coherence tomography method. The Fourier domain (optical frequency ramping) method is employed in the embodiment. The Fourier domain method uses a wavelength scanning light source 11 which scans while temporally changing the wavelength. More specifically, light emitted from the wavelength scanning light source is input through an optical fiber 12a into a first fiber coupler 13. The input light is divided in the fiber coupler 13 into a reference light and a measurement light at a ratio of 1:99, both of which lights are output. The reference light is input through an optical fiber 12b to an input section of a first circulator 14. The reference light is further output from an input/output section of the first circulator 14 through an optical fiber 12c out of an end of the optical fiber 12c. The reference light enters a reference mirror 16 through a plurality of collimator lenses 15.

The reference light reflected on the reference mirror 16 is again input through the collimator lenses 15 to the end of the optical fiber 12c. The reference light is further input through the optical fiber 12c to the input/output section. The reference light delivered from the output section of the first circulator 14 is input through the optical fiber 12d to a first input section of a second fiber coupler 17. On the other hand, the measurement light output from the first fiber coupler 13 is input through an optical fiber 12e to an input section of a second circulator 18. The measurement light is further output through an input/output section of the second circulator 18, the optical fiber 12f and the end of the optical fiber 12f. The measurement light output from an end of the optical fiber 12f is input through a collimator lens 19 to a galvanometer scanner 20. The galvanometer scanner 20 is provided for scanning the measurement light and driven by a galvanometer driver 21.

Longer wavelength side light of the measurement light output from the galvanometer scanner 20 is reflected on a hot mirror 22 at an angle of 90 degrees, whereas shorter wavelength side light is allowed to transmit through the hot mirror 22. The reflected measurement light is emitted through an objective lens 23 from the inspection window, thereby entering the subject's eye E. The measurement light incident on the subject's eye E is reflected on tissues of the anterior eye part Ec (cornea, anterior chamber, iris, crystalline lens and the like). The reflected light is output through the inspection window, the objective lens 23, the hot mirror 22, the galvanometer scanner 20 and the collimator lens 19 sequentially in this order into the end of the optical fiber 12f. The reflected light is further input through the optical fiber 12f into the input/output section of the second circulator 18. The reflected light is further output from the output section of the second circulator 18 thereby to be input through the optical fiber 12g into an input section of the second fiber coupler 17.

In the second fiber coupler 17, the reflection light from the anterior eye part Ec and the reference light input through the optical fiber 12d are multiplexed at a ratio of 50:50, for example. The obtained multiplex signal is input through optical fibers 12h and 12i to a detector 24. Coherence is measured for every wavelength by the detector 24. A measured coherence signal is input to an AD board 25 provided in the control device 3. Furthermore, the Fourier transformation and other processes are carried out for the coherence signal by an operation section 26 of the control device 3. As a result, a tomographic image of the anterior eye part Ec along the scan line is obtained.

In this case, the control device 3 sets a scan pattern for the measurement light by the galvanometer scanner 20 or a direction of the scan line (B-scan). The galvanometer driver 21 then controls the galvanometer scanner 20 based on a command signal delivered from the control device 3 (the operation section 26), as will be described in detail later. Data of obtained tomographic image of the anterior eye part Ec is processed for refractive correction and thereafter stored on the storage section 10. The obtained tomographic image T can be displayed on the monitor 7 as schematically shown in FIG. 1.

Next, the anterior eye part imaging system 6 comprises illumination sources 27, the objective lens 23, the hot mirror 22, a cold mirror 28, an imaging lens 29, a CCD camera 30 and an optics control section 31. The illumination sources 27 irradiate the front of the subject's eye with illumination light within a visible light range. Light reflected on the subject's eye E is input to the CCD camera 30 through the objective lens 23, the hot mirror 22, the cold mirror 28 and the imaging lens 29. Consequently, a frontal image F of the subject's eye E is obtained. Data of the obtained image is processed by the optics control section 31 thereby to be displayed on the monitor 7.

The alignment optics system 4 comprises a fixation lamp system, an XY-direction location detection system and a Z-direction location detection system. The fixation lamp system is provided for keeping the subject's eye immovable as long as possible by having the subject intently gaze at the fixation lamp. The XY-direction location detection system is provided for detecting an XY-direction location (displacement in upward, downward, rightward and leftward directions relative to the apparatus body) of the subject's eye E (corneal apex). The Z-direction location detection system is provided for detecting a front-back direction (the Z-direction) location of the subject's eye E (corneal apex).

The fixation lamp system comprises a fixation lamp 32, a cold mirror 33, a relay lens 34, a half mirror 35, the cold mirror 28, the hot mirror 22 and the objective lens 23. Light (green light, for example) is emitted from the fixation lamp 32 through the cold mirror 33, the relay lens 34, the half mirror 35, the cold mirror 28, the hot mirror 22 and the lens 23 sequentially in this order, thereafter being radiated from the inspection window toward the subject's eye E. The XY-direction location detection system comprises an XY-direction location detection light source 36, the cold mirror 33, the relay lens 34, the half mirror 35, the cold mirror 28, the hot mirror 22, the objective lens 23, an imaging lens 37 and a location sensor 38. The XY-direction location detection light source 36 emits alignment light for location detection. The alignment light is radiated through the cold mirror 33, the relay lens 34, the half mirror 35, the cold mirror 28, the hot mirror 22 and the objective lens 23, thereafter being radiated from the inspection window toward the anterior eye part Ec (the cornea) of the subject's eye E.

Since the corneal surface of the subject's eye E is spherical, the alignment light is reflected on the corneal surface while a bright spot image is formed inside the corneal apex of the subject's eye E. The reflected light is incident through the inspection window. The reflected light (bright spot) from the corneal apex is input through the objective lens 23, the hot mirror 22, the cold mirror 28, the half mirror 35 and the imaging lens 37 into the location sensor 38. As a result, a location of bright spot is detected by the location sensor 38, whereby the location of corneal apex (X-direction and Y-direction locations) is detected. The bright spot appears in an image taken by the CCD camera 30 (an image displayed on the monitor 7).

A detection signal of the location sensor 38 is input to the optics control section 31 and the control device 3. In this case, the location sensor 38 and the anterior eye part imaging system 6 are aligned with each other, and a predetermined (normal) image obtaining location (a location to be followed during obtainment of tomographic image) of the corneal apex is set. The image obtaining location corresponds with the center location (the center location of the screen of the monitor 7) of an image taken by the CCD camera 30, for example. Based on the detection by the location sensor 38, the control device 3 obtains X-direction and Y-direction locational displacement amounts of the detected corneal apex (bright spot) relative to the normal location or, in this case, amounts of locational displacement from the screen center of the monitor 7.

The Z-direction location detection system comprises a Z-direction location detection light source 39, an imaging lens 40 and a line sensor 41. The Z-direction location detection light source 39 irradiates the subject's eye E with detection light (slit light or spot light) diagonal from the line sensor 41. Light reflected diagonally from the corneal apex is incident through the imaging lens 40 on the line sensor 41. In this case, an incident position of the reflected light incident on the line sensor 41 differs depending upon the front-back direction (Z-direction) location of the subject's eye E relative to the apparatus body. Accordingly, the Z-direction location (distance) of the subject's eye E relative to the apparatus body is detected.

A detection signal of the line sensor 41 is input to the control device 3. Since a suitable Z-direction location of the subject's eye E relative to the apparatus body is previously set in the control device 3, the control device 3 can obtain a Z-direction displacement amount of the subject's eye E relative to the suitable location based on the result of detection by the line sensor 41.

Based on the detected X- and Y-direction location displacement amounts of the corneal apex and the detected Z-direction location displacement amount of the subject's eye E, the control device 3 controls the apparatus body 2 to move the apparatus body 2 relative to the holder so that the aforesaid location displacement amounts all become null. In this case, the control device 3 moves the apparatus body relative to the holder in starting to obtain a tomographic image so that the location of corneal apex corresponds with the predetermined image obtainment location. With this, the control device 3 moves the apparatus body during the processing of obtaining the tomographic image so that the locational relationship between the corneal apex and the apparatus body is kept constant. Thus, an alignment unit and an automatic eye tracking unit are configured as described above.

As will be described in detail in the description of the operation of the apparatus, the control device 3 controls the OCT system 5, the anterior eye part imaging system 6, the alignment optics system 4, the body drive section 2 and the like by the software configuration (execution of an anterior eye part tomography imaging program), thereby executing the processing of obtaining a tomographic image of the anterior eye part Ec. In executing the processing, the control device 3 causes the inspector (the user) to designate an area or location whose tomographic image is to be obtained, while the frontal image F of the subject's eye E imaged by the anterior eye part imaging system 6 is displayed on the monitor 7 (a designating step).

In the embodiment, the area or location is designated by the inspector who touches the touch panel 9 on the screen of the monitor 7. Accordingly, the touch panel 9 serves as a designating unit. Furthermore, the inspector can select either an entire area measurement mode in which a tomographic image of entire area of the anterior eye part Ec is obtained or an area designation mode in which part of the area of the anterior eye part Ec is obtained. When an area or location whose tomographic image to be obtained has been determined, the control device 3 sets a scan line (a scan pattern) in the OCT system 5 so that measurement light is scanned in the area designated by the OCT system 5. In this case, a direction in which the scan line extends (the B-scan direction) is set on a straight line passing the corneal apex of the subject's eye E (a setting step). Accordingly, the control device 3 serves as a scan line setting unit.

Furthermore, after the setting of the scan line, the control device 3 controls the OCT system 5 (the galvanometer scanner 20) based on the set scan line (the scan pattern) so that the obtainment of a tomographic image is carried out (a tomographic image obtaining step). When the obtainment of a tomographic image of the entire area has been selected by the inspector, the control device 3 employs a radial scan (see FIG. 6) as the scan pattern. More specifically, a tomographic image is scanned while a radial direction serves as the B-scan direction and a circumferential direction serves as the C-scan direction.

Figure 3A:
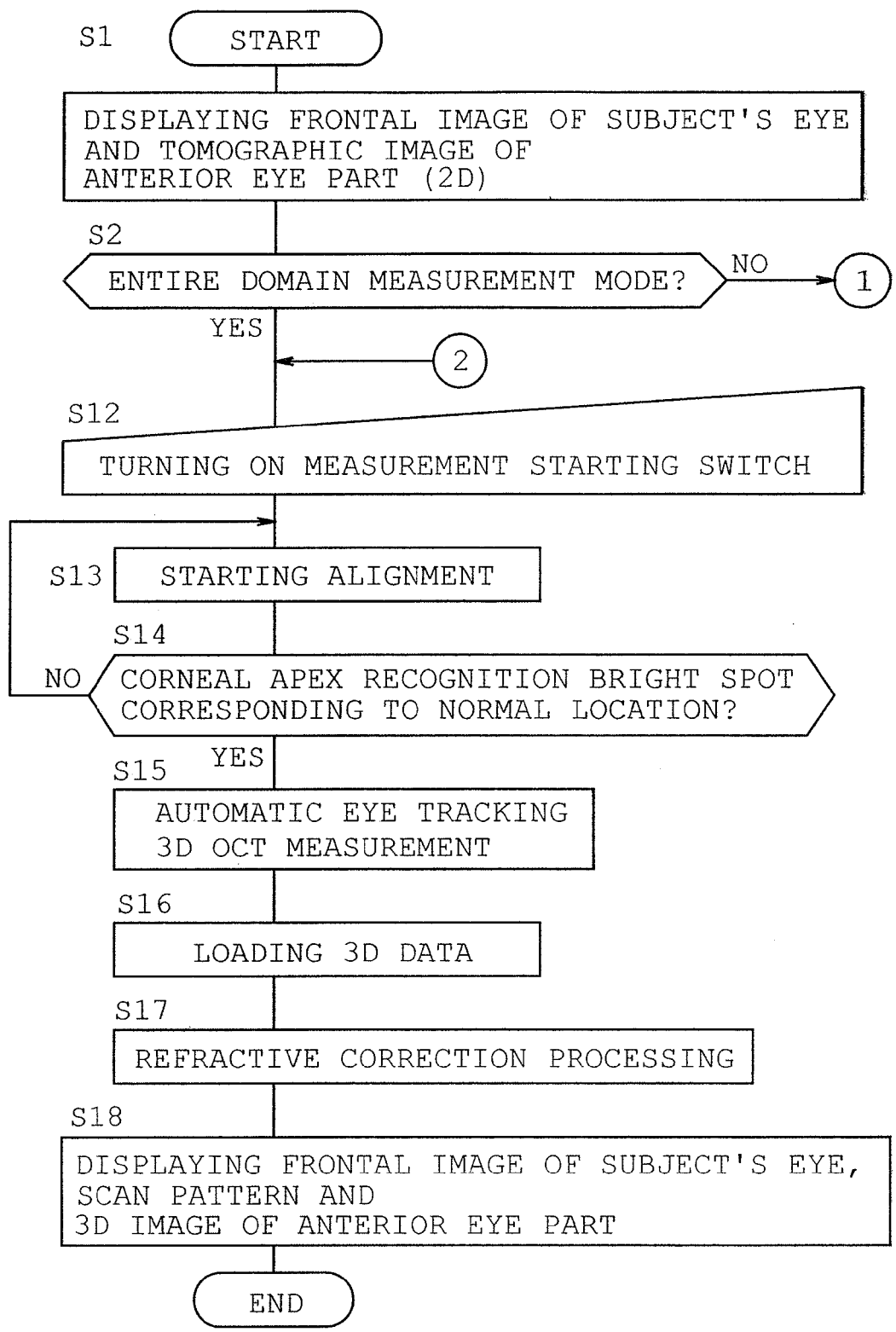
FIGS. 3A and 3B are flowcharts showing a processing procedure for obtaining a tomographic image by a control device.
Figure 3B:
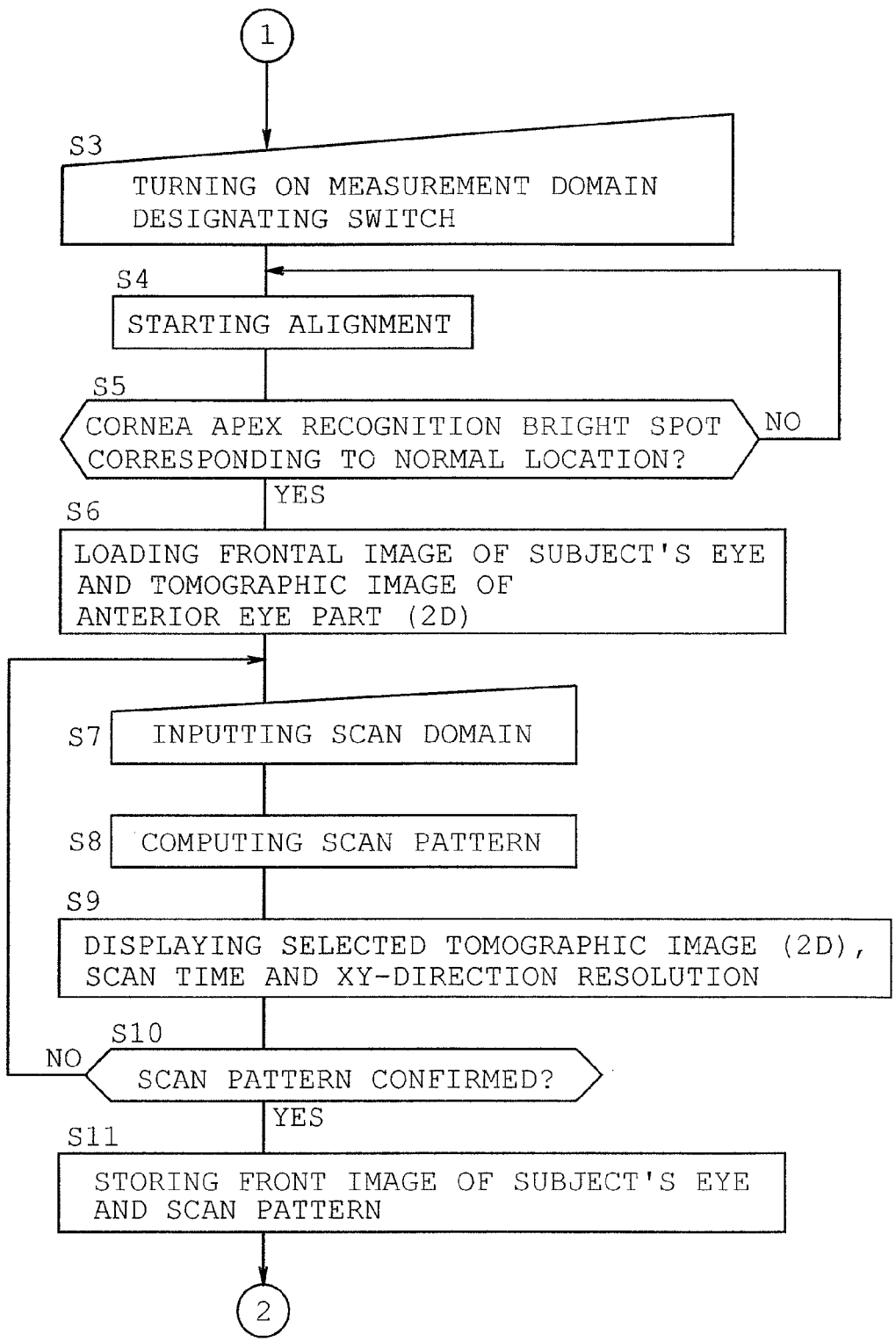
Figure 4:
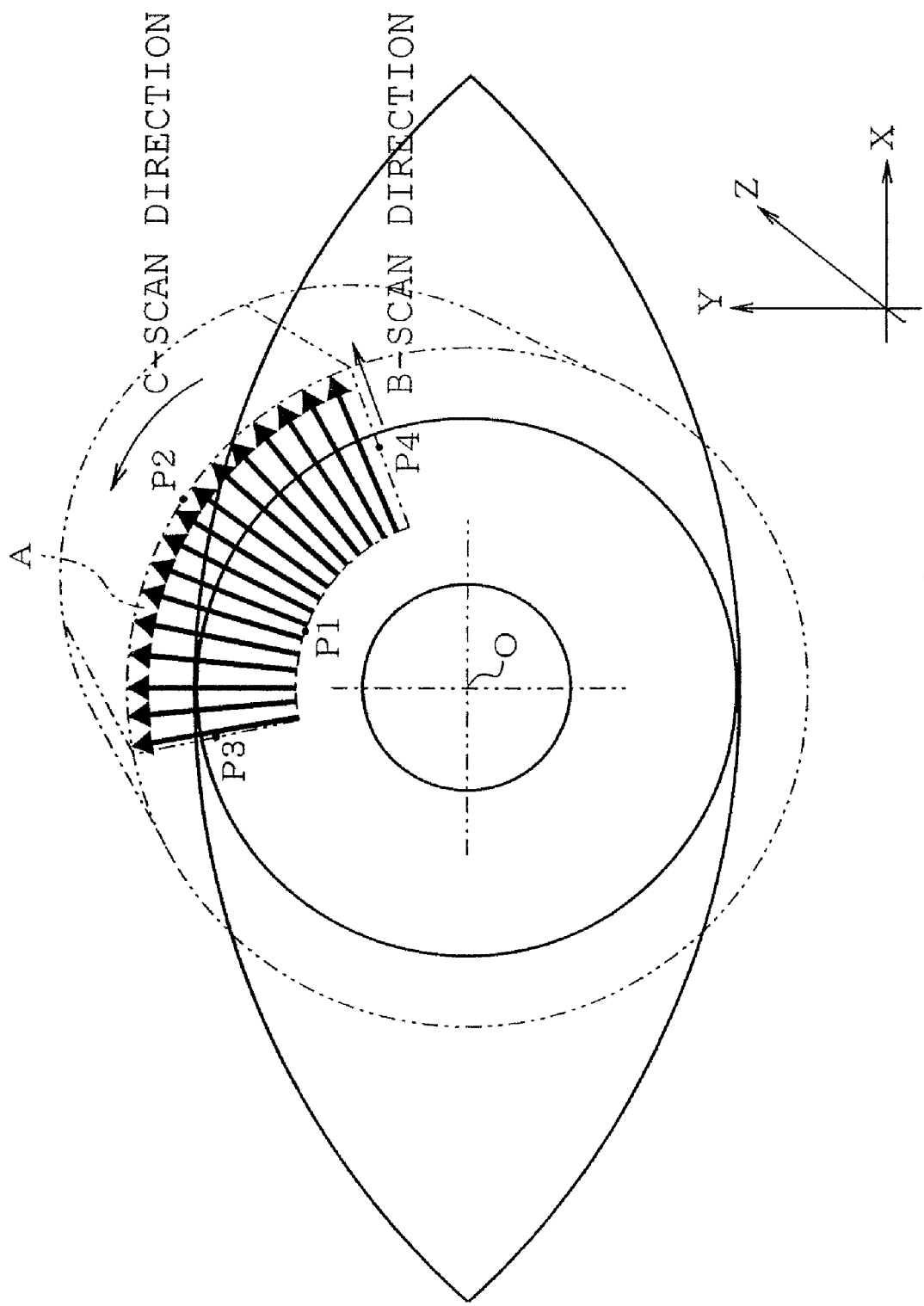
FIG. 4 is a diagrammatic view showing an example of the relationship between a frontal image of subject's eye and a scan area.

The operation of the OCT anterior eye part imaging apparatus 1 will now be described with further reference to FIGS. 3A, 3B and 4 as well as to FIGS. 1 and 2. FIGS. 3A and 3B are flowcharts showing the processing procedure executed by the control device 3 when a tomographic image of the anterior eye part Ec of the subject's eye E is obtained. The subject puts his or her jaw on the jaw support and applies the forehead pad onto his or her forehead, so that the subject's eye E is located in front of an imaging inspection window provided in the front of the apparatus body. The processing of obtaining a tomographic image of the anterior eye part Ec starts or the OCT anterior eye part imaging program starts up in this state. Firstly, in step S1, a current frontal image of the subject eye E imaged by the anterior eye part imaging system 6 (the CCD camera 6) is displayed on the monitor 7. With this, a current tomographic image of the anterior eye part Ec is obtained by scanning along a scan line horizontally extending through the screen center, being also displayed on the monitor 7 (see FIG. 2). However, the displayed frontal image and tomographic image are not loaded onto a memory at this stage of the processing.

In step S2, it is determined whether the entire area measurement or the area designation mode should be executed. A tomographic image of the entire are of the anterior eye part Ec is obtained in the entire area measurement mode, whereas part of the area of the anterior eye part Ec is obtained in the area designation mode. In the embodiment, when a measurement area designating switch of the key operation section 8 or on the touch panel 9 is turned on (step S3), it is determined that the area designation mode has been selected (NO in step S2). On the other hand, when a measurement start switch is turned on without turn-on of the measurement area designating switch (step S12), it is determined that the entire area measurement mode has been selected (YES in step S2). Accordingly, when wishing to obtain a tomographic image of a part of the anterior eye part Ec, the inspector (the operator) turns on the measurement area designation switch. When wishing to obtain a tomographic image of the entire anterior eye part Ec, the inspector turns on the measurement start switch without operation of the measurement area designation switch.

Suppose now that the inspector wishes to obtain a 3D image of a corner of the anterior eye part Ec for diagnosis of glaucoma, for example. In this case, the corner which is a part of the anterior eye part Ec is considered to be abnormal. In this case, the measurement area designating switch of the key operation section 8 is turned on (step S3). X-, Y- and Z-direction alignments are initiated by the alignment optics system 4 and the like. When the bright spot for recognition of the corneal apex corresponds with the normal location (the center location of an image taken by the CCD camera 30) (YES in step S5), the alignments are completed. In step S6, data of a frontal image of the subject's eye E taken by the anterior eye part imaging system 6 at the time of or before completion of the alignment is loaded onto the memory. With this, data of a tomographic image of the anterior eye part Ec obtained by scanning along the horizontal scan line is also loaded onto the memory.

The inspector enters (designates) a scan area whose tomographic image is to be obtained, in step S7. In the entering operation, the touch panel 9 is touched by the inspector while the frontal image of the subject's eye E is displayed on the monitor 7. FIG. 4 shows a specific example of scan area A. In the example, the scan area A is set as an arcuately spread plane including an upper right part of a peripheral edge of iris as viewed in FIG. 4. In this case, four points, that is, an inner circumference side point P1, an outer circumference side point P2 and two points P3 and P4 on both circumferential sides respectively are designated (touched), whereby the scan area A is input.

Various manners can be employed other than the above-described manner regarding the operation of designating the scan area. For example, a square frame encircling the scan area may be designated in one manner. Four apexes of the scan area may be designated in another manner. A center point of the scan area and size (upward, downward, rightward and leftward spread) may be designated in further another manner. Additionally, the scan area should not be limited to a relatively wider area. The inspector can designate a specific location and a relatively narrower area around the designated location.

When the scan area A has been input, a scan pattern for the scan area A is obtained by computation in step S8. Scan lines with respect to the B-scan direction and a location (range) with respect to the C-scan direction are set as the scan pattern. In this case, each scan line is set so as to radially extend on a straight line passing the corneal apex. In FIG. 4, each scan line shown as bold arrow is set so as to extend along the straight line passing the corneal apex.

When the scan pattern has bee obtained, a tomographic image along one scan line of the selected area (for example, the circumferential center of the scan area A) is scanned by the OCT system 5 to be displayed on the monitor 7, in step S9. With this, a necessary scanning time and X- and Y-direction resolutions are obtained by computation to be displayed on the monitor 7. When confirming the displayed contents on the monitor 7, the inspector determines whether the displayed contents should be employed or whether the scan area A should be re-designated. The inspector then operates the key operation section to input "YES" or "NO" (step S10).

In the case of "NO" (NO in step S10), the control sequence returns to step S7 so that the processing is re-executed from the designation of scan area. On the other hand, when "YES" has been input (YES in step S10), data of the frontal image of the subject's eye E and the scan pattern are stored. Subsequently, when the inspector turns on the measurement start switch (step S12), the X-, Y- and Z-direction alignments are initiated by the alignment optics system 4 and the like in step S13. When the bright spot for recognition of the corneal apex corresponds with the normal location (YES in step S14), the alignments are completed. In step S15, the processing is carried out to obtain a tomographic image of the anterior eye part Ec from the set scan area by the OCT system 15. An automatic eye tracking functions during the processing, whereby the apparatus body is moved by the alignment system 4 and the like so that the bright spot for recognition of the corneal apex corresponds with the normal location (the center location of the image taken by the CCD camera 30).

Figure 6A:
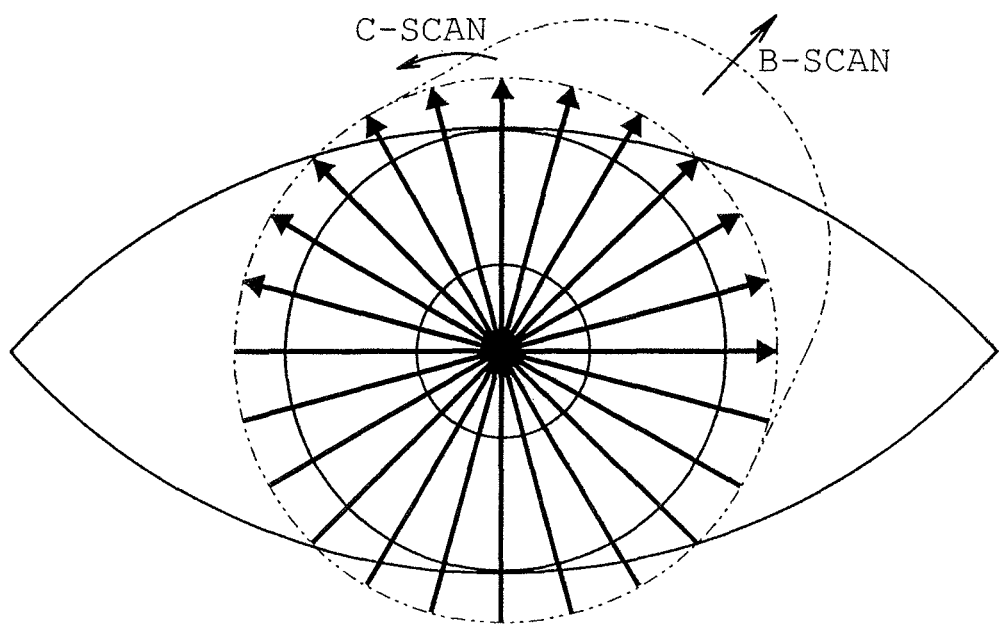
FIG. 6A is a diagrammatic view showing a radial scan system in the OCT.
Figure 6B:
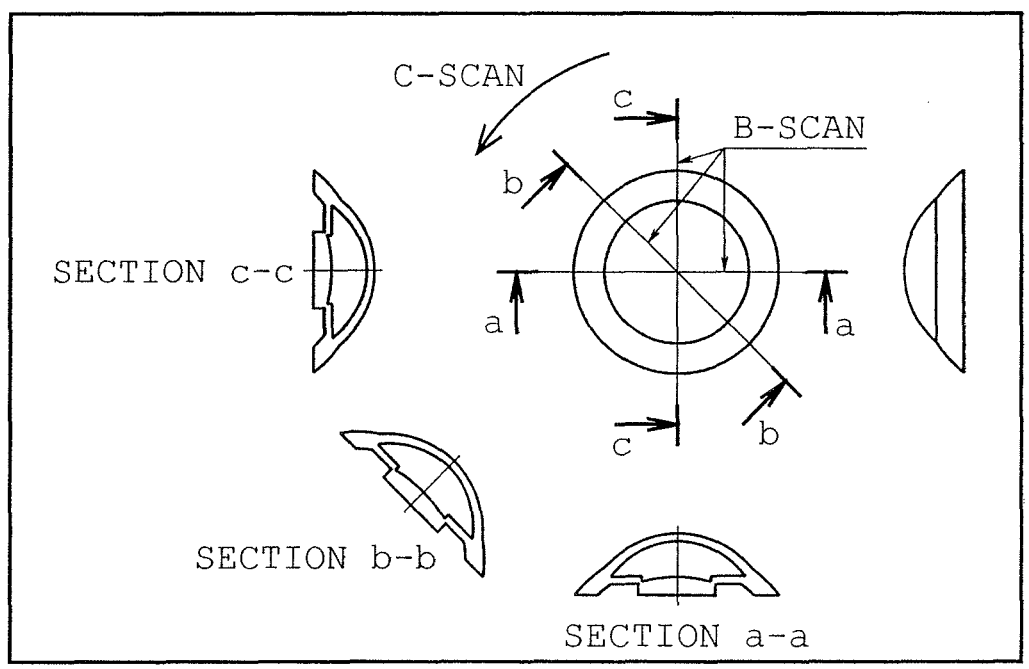
FIG. 6B illustrates a tomographic image obtained by the radial scan manner.

The processing to obtain the tomographic image in step S15 is executed in accordance with the set scan pattern (scan lines) when the scan area has been set. Furthermore, when the entire area of the anterior eye part Ec is measured (YES in step S8), a tomographic image of the entire area of the anterior eye part Ec is obtained by the radial scan method as shown in FIG. 6. In this case, the locational relationship between the apparatus body and the subject's eye is kept constant by the automatic eye tracking. As a result, even when the subject's eye E is displaced, each scan line can be prevented from being displaced from the straight line passing the corneal apex. In step S16, data of the tomographic image obtained along each scan line is loaded onto the memory.

The refractive correction is carried out for the data of each tomographic image in step S17. More specifically, since measurement light is refracted on the substantially spherical cornea (on the corneal surface and boundary surface between the cornea and anterior chamber), the obtained tomographic image is distorted more or less. Accordingly, the image data is corrected with respect to the corneal refraction. Corrected image data is stored on the storage section 10, and the frontal image of the subject eye E, the scan pattern and the 3D image of the anterior eye part are displayed on the monitor 7. The processing is then completed.

Figure 5A:
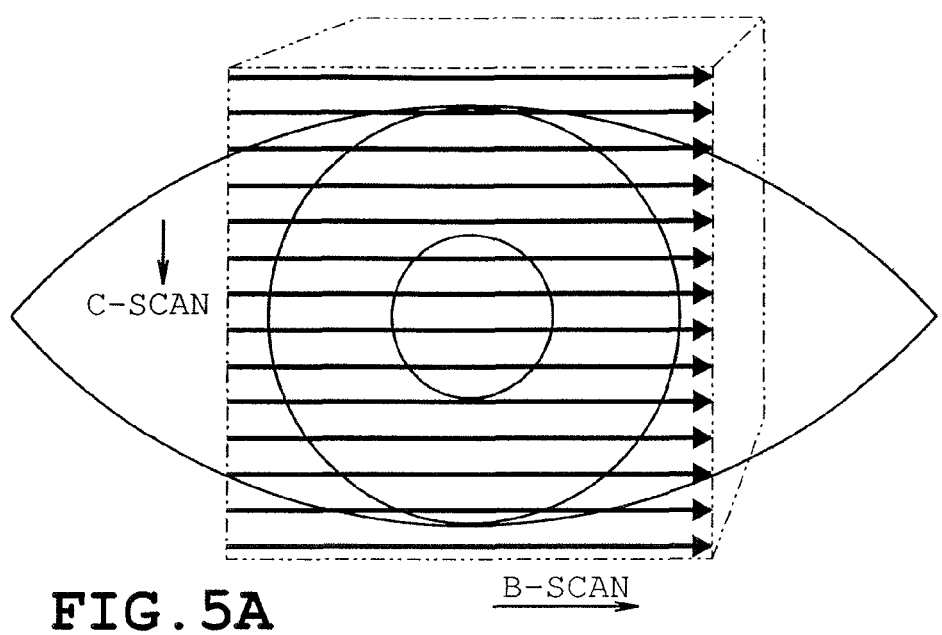
FIG. 5A is a diagrammatic view showing a raster scan manner in the OCT.
Figure 5B:
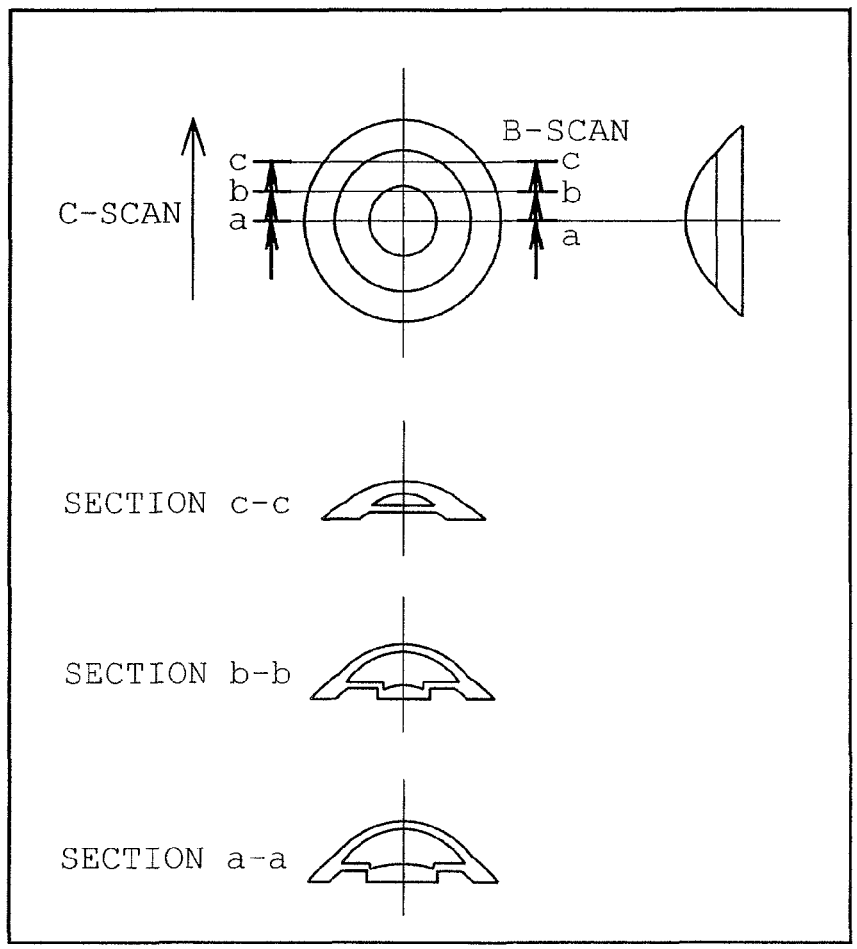
FIG. 5B illustrates a tomographic image obtained by the raster scan system.

When the scan line (B-scan direction) extends in the X-direction (the horizontal direction) as in the raster scan (see FIG. 5), for example, the B-scan direction tomographic image is affected by both X- and Y-direction refractions unless the scan line passes the corneal apex. Accordingly, a relatively troublesome time-consuming correction has conventionally been necessitated after obtainment of a 3D image by the C-scan.

In the embodiment, however, the measurement light on the straight line passing the corneal apex is vertically incident on the cornea. As a result, a B-scan direction tomographic image along the scan line located on the straight line passing the corneal apex is two-dimensionally affected by the corneal refraction only in the plane thereof. Thus, the correction of corneal refraction in step S17 needs to be executed once for one tomographic image regardless of other tomographic images. Consequently, the refraction correction can easily be carried out in a relatively shorter time period with high precision.

According to the foregoing embodiment, the OCT corneal eye imaging apparatus includes the OCT system 5, the corneal eye imaging system 6 and the alignment optics system 4. The location relationship between the corneal apex of the subject's eye E and the apparatus body and accordingly the OCT system 5 can be kept constant. Furthermore, the inspector can designate the scan area whose tomographic image is to be obtained on the frontal image of the subject's eye E displayed on the monitor 7. With this, the scan line (B-scan direction) in the OCT system 5 is set on the straight line passing the corneal apex. Consequently, a time period necessary for the imaging by the OCT system can be rendered shorter without reduction in the resolution. Accordingly, the burden imposed on the subject can be rendered smaller and the influences of involuntary eye movement can also be reduced. Moreover, the correction of the B-scan direction tomographic image can easily be carried out in a relatively shorter time period on the basis of only one tomographic image. Furthermore, particularly in the foregoing embodiment, the scan area can be designated when the inspector touches the touch panel provided on the surface of the motor 7. Consequently, the scan area can be designated easily and reliably. Furthermore, since the OCT system 5 obtains the tomographic image by the Fourier domain method, the imaging time period can further be shortened.

The OCT system 5 employs the Fourier domain method in the foregoing embodiment. However, when the time domain method is employed, instead of the Fourier domain method, the OCT corneal eye imaging apparatus can be operated in the same manner as described above and can achieve the same effect as described above. The OCT system may be configured without use of optical fiber. Furthermore, the designating unit should not be limited to the touch panel. For example, a keyboard or joystick may be employed, instead of the touch panel. Additionally, it is possible to provide various modified forms of hardware configurations (configuration and arrangement of mirrors and lenses).

In the foregoing embodiment, the subject's eye E is irradiated with alignment light, and the light reflected on the corneal apex (the bright spot) is input to the location sensor 38 so that the location of corneal apex is detected. However, the corneal apex location detecting unit may be configured so as to detect the location of corneal apex using a anterior eye part frontal image or a tomographic image.

In the foregoing embodiment, the automatic eye tracking function is canceled during execution of steps S7 to S11 executed for the frontal image of the subject's eye E obtained in step S6 and the tomographic image of the anterior eye part Ec (displayed as a static image on the monitor 7). However, the automatic eye tracking function may normally be in operation, instead. In this case, steps S7 to S11 can be carried out while the frontal image of the subject's eye E obtained in step S6 and the tomographic image of the anterior eye part Ec are displayed on the monitor 7 in real time. Furthermore, the alignment at each of steps S13 and S14 can be carried out in a shorter time period.

The foregoing description and drawings are merely illustrative of the principles of the present invention and are not to be construed in a limiting sense. Various changes and modifications will become apparent to those of ordinary skill in the art. All such changes and modifications are seen to fall within the scope of the invention as defined by the appended claims.

What is claimed is:

1. An optical anterior eye part imaging apparatus for ophthalmic examination, comprising:
    a holder;
    an apparatus body mounted on the holder;
    a tomographic image obtaining unit that is provided on the apparatus body and is configured to obtain a tomographic image of subject's anterior eye part in a depth direction by optical coherence tomography, the tomographic image being taken along a scan line;
    an imaging unit that is provided on the apparatus body and is configured to image a frontal image of the subject's eye;
    a display unit that is configured to display the image of the subject's eye obtained by the imaging unit;

a corneal apex location detecting unit that is configured to detect a location of a corneal apex of the subject's eye;

an alignment unit that is configured to move the apparatus body relative to the holder so that the location of the corneal apex corresponds with a predetermined image obtaining location;

a designating unit that is configured to designate an area or a location whose tomographic image is to be obtained on the subject's frontal image displayed on the display unit; and a scan line setting unit that is configured to set a scan line in the tomographic image obtaining unit on a straight line passing the corneal apex according to the area or location designated by the designating unit.

2. The apparatus according to claim 1, further comprising an automatic eye tracking unit that moves the apparatus body so that a predetermined locational relationship is maintained between the corneal apex and the apparatus body during the obtainment of the tomographic image by the tomographic image obtaining unit.

3. The apparatus according to claim 1, wherein the designating unit comprises a touch panel provided on a screen of the display unit.

4. The apparatus according to claim 2, wherein the designating unit comprises a touch panel provided on a screen of the display unit.

5. A method of obtaining a tomographic image of an anterior eye part of subject's eye for ophthalmic examination by the use of an anterior eye part imaging apparatus, said apparatus including a holder, an apparatus body mounted on the holder, a tomographic image obtaining unit that is provided on the apparatus body and is configured to obtain a tomographic image of subject's anterior eye part in a depth direction by optical coherence tomography, the tomographic image being taken along a scan line; an imaging unit that is provided on the apparatus body and is configured to image a frontal image of the subject's eye; a display unit that is configured to display the image of the subject's eye obtained by the imaging unit; a corneal apex location detecting unit that is configured to detect a location of a corneal apex of the subject's eye; and an alignment unit that is configured to move the apparatus body relative to the holder so that the location of the corneal apex corresponds with a predetermined image obtaining location, the method comprising:

receiving input designating an area or a location whose tomographic image is to be obtained while the subject's frontal image is displayed on the display unit;

setting, in an automatic manner, a scan line in the tomographic image obtaining unit on a straight line passing the corneal apex according to the area or location designated by the input; and obtaining a tomographic image by the tomographic image obtaining unit based on the scan line set in the scan line setting step.

6. The method according to claim 5, wherein the tomographic image obtaining step includes moving the apparatus body by an automatic eye tracking unit so that a predetermined positional relationship is maintained between the corneal apex and the apparatus body during the obtainment of the tomographic image by the tomographic image obtaining unit.

7. The method according to claim 5, wherein the receiving step includes receiving the input via a touch panel provided on a screen of the display so that an area or location whose tomographic image is to be obtained on the subject's frontal image displayed on the display unit is directly designated.

8. The method according to claim 6, wherein the receiving step includes receiving the input via a touch panel provided on a screen of the display so that an area or location whose tomographic image is to be obtained on the subject's frontal image displayed on the display unit is directly designated.

* * * * *